(12) United States Patent
Black et al.

(10) Patent No.: US 10,724,945 B2
(45) Date of Patent: Jul. 28, 2020

(54) LASER DETECTION SYSTEM AND METHOD

(71) Applicant: CASCADE TECHNOLOGIES HOLDIGS LIMITED, Stirling (GB)

(72) Inventors: Paul Black, Stirling (GB); Ruth Lindley, Stirling (GB)

(73) Assignee: CASCADE TECHNOLOGIES HOLDINGS LIMITED (GB)

(*) Notice: Subject to any disclaimer, the term of this patent is extended or adjusted under 35 U.S.C. 154(b) by 0 days.

(21) Appl. No.: 15/132,993

(22) Filed: Apr. 19, 2016

(65) Prior Publication Data

US 2017/0299503 A1    Oct. 19, 2017

(51) Int. Cl.
*G01N 21/31* (2006.01)
*G01N 21/39* (2006.01)
(Continued)

(52) U.S. Cl.
CPC ......... *G01N 21/31* (2013.01); *G01N 21/3504* (2013.01); *G01N 21/39* (2013.01);
(Continued)

(58) Field of Classification Search
CPC .... G01N 21/31; G01N 21/39; G01N 21/3504; G01N 2201/06113; G01N 33/0037; G01N 2201/068; G01N 2021/399; G01N 21/05; G01N 21/031; G01N 21/35; G01N 2021/3595; G01N 33/004; G01N 2201/0697; G01N 2021/6417; G01N 2201/129; G01N 33/0006; G01N 21/3581; G01N 2021/6421; G01N 21/4795; G01N 2021/1704; G01N 2021/6463; G01N 2021/151; G01N 21/6402; G01N 27/4074; G01N 30/74; G01N 2021/6419;
(Continued)

(56) References Cited

U.S. PATENT DOCUMENTS 2,844,730 A * 7/1958 Tandler .................. G01J 5/601
                                                        250/339.04
3,792,272 A 2/1974 Harte et al.
(Continued)

FOREIGN PATENT DOCUMENTS

CN    104155241    11/2014
DE    19716061    3/1998
(Continued)

OTHER PUBLICATIONS

Official Action for U.S. Appl. No. 15/133,517, dated Jun. 29, 2017 17 pages.
(Continued)

*Primary Examiner* — Mohamed K Amara
(74) *Attorney, Agent, or Firm* — Sheridan Ross P.C.

(57) ABSTRACT

A laser detection system comprises a plurality of lasers wherein each laser is configured to produce a respective laser beam for excitation of one or more different compounds, a sample cell for containing a volume of sample gas, at least one directing device configured to direct the laser beams to the sample cell, wherein the at least one directing device is configured to direct the laser beams along a common optical path to the sample cell, and a detector apparatus for detecting light output from the cell.

24 Claims, 3 Drawing Sheets

(51) Int. Cl.
*G01N 21/3504* (2014.01)
*G01N 33/00* (2006.01)

(52) U.S. Cl.
CPC ... *G01N 33/0037* (2013.01); *G01N 2201/068* (2013.01); *G01N 2201/06113* (2013.01); *Y02A 50/245* (2018.01)

(58) Field of Classification Search
CPC ... G01N 2021/8578; G01N 2021/1795; G01N 2201/0696; G01N 21/3586; G01N 33/0042
See application file for complete search history.

(56) References Cited

U.S. PATENT DOCUMENTS

| | | | |
|---|---|---|---|
| 3,851,213 A * | 11/1974 | Van Dam | G01J 3/10 313/599 |
| 4,496,839 A * | 1/1985 | Bernstein | G01N 21/6402 250/253 |
| 4,598,201 A * | 7/1986 | Fertig | G01N 21/37 250/252.1 |
| 4,707,133 A * | 11/1987 | Roberts | G01N 21/39 250/565 |
| 4,927,265 A * | 5/1990 | Brownlee | G01N 21/31 204/603 |
| 5,076,699 A * | 12/1991 | Ryan | G01J 3/26 250/338.1 |
| 5,202,570 A * | 4/1993 | Tanaka | G01N 21/39 250/205 |
| 5,373,160 A * | 12/1994 | Taylor | G01N 21/39 250/338.5 |
| 5,407,638 A * | 4/1995 | Wang | G01N 21/05 250/576 |
| 5,451,787 A | 9/1995 | Taylor | |
| 5,625,189 A | 4/1997 | McCaul et al. | |
| 5,751,419 A * | 5/1998 | Takahashi | G02B 26/04 356/321 |
| 5,760,895 A | 6/1998 | Kebabian | |
| 5,896,088 A * | 4/1999 | Brooks, Jr. | G01N 21/3504 250/338.5 |
| 5,900,632 A * | 5/1999 | Sterling | G01N 21/71 250/252.1 |
| 5,923,035 A * | 7/1999 | Winkler | G01J 3/10 250/338.5 |
| 6,025,597 A * | 2/2000 | Sterling | A61B 5/14532 250/339.03 |
| 6,184,535 B1 * | 2/2001 | Kashima | G01N 21/6428 250/458.1 |
| 6,420,695 B1 * | 7/2002 | Grasdepot | G01J 3/26 250/226 |
| 6,545,278 B1 | 4/2003 | Mottier et al. | |
| 6,560,545 B2 * | 5/2003 | Stedman | G01N 21/3504 250/338.5 |
| 6,657,198 B1 | 12/2003 | May | |
| 6,723,989 B1 * | 4/2004 | Didomenico | G01N 21/33 250/338.5 |
| 6,885,965 B2 * | 4/2005 | Butler | G01J 3/28 356/451 |
| 6,927,393 B2 * | 8/2005 | Cotte | G01N 21/359 250/336.1 |
| 6,983,639 B1 * | 1/2006 | Didomenico | G01N 21/33 73/23.31 |
| 7,141,793 B2 * | 11/2006 | Johnson | G01N 21/3504 250/338.5 |
| 7,326,930 B2 * | 2/2008 | Crawely | G01J 3/4338 250/341.1 |
| 7,352,463 B2 | 4/2008 | Bounaix | |
| 7,483,192 B2 * | 1/2009 | Ulbricht | G01N 21/3504 359/199.1 |
| 7,498,575 B2 * | 3/2009 | Huebner | G01N 21/3504 250/338.1 |
| 7,590,156 B1 | 9/2009 | Richardson et al. | |
| 7,605,370 B2 * | 10/2009 | Russell | G01J 3/02 250/339.07 |
| 7,679,047 B2 * | 3/2010 | Yoshida | G01N 21/3504 250/252.1 |
| 7,800,751 B1 | 9/2010 | Silver et al. | |
| 7,835,005 B2 * | 11/2010 | Appel | G01N 21/274 356/437 |
| 7,898,665 B2 * | 3/2011 | Brukilacchio | A61B 1/0653 356/417 |
| 8,269,971 B1 | 9/2012 | Marsh et al. | |
| 8,686,364 B1 | 4/2014 | Little et al. | |
| 9,316,577 B1 | 4/2016 | Doggett | |
| 2003/0071218 A1 | 4/2003 | Nakamura et al. | |
| 2003/0152307 A1 | 8/2003 | Von Drasek et al. | |
| 2003/0218750 A1 | 11/2003 | Friberg et al. | |
| 2006/0058682 A1 * | 3/2006 | Miller | A61B 3/102 600/476 |
| 2007/0082407 A1 | 4/2007 | Littlel, III | |
| 2007/0098028 A1 * | 5/2007 | Alcock | G02B 6/4214 372/29.015 |
| 2007/0230520 A1 * | 10/2007 | Mordaunt | A61F 9/008 372/23 |
| 2008/0135760 A1 | 6/2008 | May | |
| 2008/0198027 A1 | 8/2008 | Bugge | |
| 2008/0234670 A1 * | 9/2008 | Rogers | A61N 5/06 606/12 |
| 2010/0195096 A1 * | 8/2010 | Schlezinger | G01N 21/894 356/237.5 |
| 2010/0228688 A1 * | 9/2010 | Little | G01N 21/359 705/413 |
| 2010/0230593 A1 | 9/2010 | Hill | |
| 2010/0284017 A1 | 11/2010 | Reyes et al. | |
| 2011/0176068 A1 * | 7/2011 | Miller | G02B 26/101 348/745 |
| 2011/0235045 A1 * | 9/2011 | Koerner | G02B 21/0056 356/451 |
| 2011/0278472 A1 * | 11/2011 | Atzler | G01J 3/0291 250/459.1 |
| 2012/0037326 A1 * | 2/2012 | Ublacker | G01N 21/15 162/198 |
| 2012/0182555 A1 | 7/2012 | Statz et al. | |
| 2013/0100451 A1 * | 4/2013 | Hager | G01N 21/532 356/438 |
| 2013/0319110 A1 | 12/2013 | Otera | |
| 2014/0077083 A1 | 3/2014 | Birnkrant et al. | |
| 2014/0160479 A1 * | 6/2014 | Hager | G01N 21/3504 356/438 |
| 2014/0204382 A1 | 7/2014 | Christensen | |
| 2015/0138533 A1 * | 5/2015 | Bolles | G01J 3/427 356/51 |
| 2015/0177131 A1 | 6/2015 | Liu et al. | |
| 2015/0241339 A1 | 8/2015 | Maksyutenko et al. | |
| 2015/0285679 A1 * | 10/2015 | Kasiutsich | G01N 21/3504 356/402 |
| 2016/0084710 A1 | 3/2016 | Keller et al. | |
| 2016/0170218 A1 * | 6/2016 | Johnson | G02B 6/32 359/356 |
| 2017/0045450 A1 * | 2/2017 | Lieber | G01N 21/645 |
| 2017/0307519 A1 | 10/2017 | Black et al. | |
| 2018/0202926 A1 | 7/2018 | Black et al. | |

FOREIGN PATENT DOCUMENTS

| | | |
|---|---|---|
| DE | 102005032722 | 10/2006 |
| DE | 102007038943 | 2/2009 |
| EP | 0768523 | 4/1997 |
| EP | 768523 | 4/1997 |
| EP | 0896216 | 2/1999 |
| EP | 896216 | 2/1999 |
| EP | 994340 | 4/2000 |
| EP | 0994340 | 4/2000 |
| EP | 1193488 | 4/2002 |
| EP | 1605251 | 12/2005 |
| EP | 1734347 | 12/2006 |
| EP | 1783481 | 5/2007 |
| EP | 1836479 | 9/2007 |
| EP | 1972922 | 9/2008 |

(56) References Cited

FOREIGN PATENT DOCUMENTS

| EP | 2375237 | 10/2011 |
|---|---|---|
| EP | 2607891 | 6/2013 |
| EP | 2927668 | 10/2015 |
| EP | 2344862 | 2/2016 |
| EP | 2993461 | 3/2016 |
| FR | 2735236 | 12/1996 |
| FR | 2971587 | 8/2012 |
| FR | 3009655 | 2/2015 |
| GB | 2389177 | 12/2003 |
| GB | 2391310 | 2/2004 |
| GB | 2401679 | 11/2004 |
| GB | 2493833 | 2/2013 |
| GB | 2497295 | 6/2013 |
| WO | WO 95/26497 | 10/1995 |
| WO | WO 00/73768 | 12/2000 |
| WO | WO 03/046522 | 6/2003 |
| WO | WO 2004/023114 | 3/2004 |
| WO | WO 2004/113169 | 12/2004 |
| WO | WO 2006/022550 | 3/2006 |
| WO | WO 2006/029920 | 3/2006 |
| WO | WO 2006/061681 | 6/2006 |
| WO | WO 2006/127722 | 11/2006 |
| WO | WO 2008/048994 | 4/2008 |
| WO | WO 2008/079032 | 7/2008 |
| WO | WO 2009/052157 | 4/2009 |
| WO | WO 2009/105571 | 8/2009 |
| WO | WO 2009/155459 | 12/2009 |
| WO | WO 2010/024756 | 3/2010 |
| WO | WO 2012/050696 | 4/2012 |
| WO | WO 2012/093952 | 7/2012 |
| WO | WO 2012/151358 | 11/2012 |
| WO | WO 2012/151678 | 11/2012 |
| WO | WO 2013/188914 | 12/2013 |
| WO | WO 2014/033465 | 3/2014 |
| WO | WO 2014/162536 | 10/2014 |
| WO | WO 2015/33582 | 3/2017 |

OTHER PUBLICATIONS

Official Action for U.S. Appl. No. 15/133,517, dated Feb. 9, 2018 16 pages.
International Search Report and Written Opinion for International (PCT) Patent Application No. PCT/GB2017/051068, dated Jun. 20, 2017, 14 pages.
International Search Report and Written Opinion for International (PCT) Patent Application No. PCT/GB2017/051078, dated Jul. 12, 2017, 16 pages.
Notice of Allowance for U.S. Appl. No. 15/133,517, dated Jun. 15, 2018 8 pages.
Lackner et al. "Demonstration of methane spectroscopy using a vertical-cavity surface-emitting laser at 1.68 μm with up to 5 MHz repetition rate," Measurement Science and Technology, Jan. 2003, vol. 14, No. 1, pp. 101-106.
International Search Report and Written Opinion for International (PCT) Patent Application No. PCT/GB2018/050148, dated Apr. 6, 2018, 19 pages.
Notice of Allowance for U.S. Appl. No. 15/133,517, dated Sep. 6, 2018 8 pages.
Official Action for U.S. Appl. No. 15/581,153, dated Aug. 16, 2018 27 pages.
Official Action for U.S. Appl. No. 15/581,153, dated May 30, 2019, 22 pages.

* cited by examiner

LASER DETECTION SYSTEM AND METHOD

BACKGROUND

Continuous emission monitoring instruments are increasingly needed to monitor industrial pollution output in various industrial sites, for example at power plants, process industry factories and commercial shipping facilities. The need arises, for example, from efficiency improvements, health and safety considerations and legislative requirements. It can be desirable to obtain measurements on a range of emitted compounds, for example: sulphur dioxide, nitrogen oxides, carbon monoxide, carbon dioxide, methane, water and oxygen.

Known gas analysis systems are sensitive to single compounds or a small number of compounds. To cover multiple compounds using known systems it can be necessary to install several different continuous emission monitoring instruments, which can be inefficient, complicated and take up significant amount of space.

SUMMARY

In a first aspect of the invention, there is provided a laser detection system comprising: a plurality of lasers wherein each laser is configured to produce a respective laser beam for excitation of one or more different compounds; a sample cell for containing a volume of sample gas; at least one directing device configured to direct the laser beams to the sample cell, wherein the at least one directing device is configured to direct the laser beams along a common optical path to the sample cell, and a detector apparatus for detecting light output from the cell.

The at least one directing device may comprise a plurality of optical components arranged such that, for each laser beam a respective at least one of the optical components is arranged to direct said laser beam along the common optical path.

The plurality of optical components may be arranged substantially in a straight line.

The plurality of optical components may be arranged such that on the common optical path the laser beams may overlap by at least 90% of their diameters, optionally at least 50% of their diameters, optionally at least 20% of their diameters, optionally at least 10% of their diameters. The laser beams may comprise infra-red light or visible light or light of any other suitable wavelength or from any suitable part of the electromagnetic spectrum Each of the lasers may be arranged such that in operation each of the lasers transmits its laser beam to its corresponding at least one of the optical components in a direction substantially orthogonal to said straight line. At least one, optionally each, of the lasers may comprise a quantum cascade laser.

At least one of the optical components may comprise a flat or non-wedged optical component, optionally each of the optical components may comprise a respective flat or non-wedged optical component.

The plurality of optical components may comprise at least one mirror, optionally at least one partially reflective mirror and/or at least one dichroic mirror.

Each of the optical components may have a thickness in a range 0.1 mm to 1 mm.

The optical components may be arranged in series and may be configured such that in operation each optical component directs a laser beam from its associated laser to join said common optical path, and/or directs or allows passage of laser beam(s) from preceding optical components in the series along said common optical path.

At least one, optionally each, of the optical components may be at least partially reflective and at least partially transmissive.

The at least one directing device may comprise steering optics between the last of said plurality of optical components and the sample cell and configured to direct the laser beams into the optical cell.

The detection apparatus may comprise a plurality of detectors, each detector being configured to detect radiation of a respective wavelength or range of wavelengths.

The system may further comprise:
a controller configured to control operation of the plurality of lasers such that the laser beams are pulsed laser beams interleaved in time.

The controller may be configured to synchronise operation of the detection apparatus and the lasers, thereby to obtain a series of detection signals, each detection signal being associated with a respective one of the lasers.

The controller may be configured to control operation of the lasers such that each laser beam is pulsed at a rate in a range 1 kHz to 200 kHz, optionally in a range 10 kHz to 100 kHz, and/or wherein the controller is configured to control the lasers such that each laser beams is pulsed with pulse lengths in a range 100 ns to 5000 ns.

The system may further comprise a processing resource configured to determine an amount of NOx based on the detected light outputs.

The plurality of compounds may comprise at least one of: NO, $NO_2$, $H_2O$, CO, $CO_2$, $CH_4$, $SO_2$, $NH_3$, $C_2H_2$, and $O_2$.

Each of the plurality of lasers may be configured to produce infrared laser radiation.

Each of the lasers may be configured to produce a laser beam of a respective different wavelength or range of wavelengths.

At least one, optionally each, of the ranges of wavelengths may be selected from the following ranges: 5.2632 to 5.2356 µm; 6.1538 to 6.1162 µm; 4.4742 to 4.4743 µm; 7.4627 to 7.4349 µm; 0.7605 to 0.7599 µm; and 10.0 to 10.2 µm.

The detector apparatus may be arranged on the opposite side of the sample cell to the plurality of lasers and the at least one directing device.

The system may further comprise a gas supply arrangement configured to supply sample, optionally a remote sample gas, to the sample cell.

The sample cell may comprise at least one of a Herriot cell, a multi-pass cell.

The system may be a continuous emission monitoring system.

In a further aspect of the invention, which may be provided independently, there is provided a method of detecting a plurality of different compounds, comprising producing a plurality of laser beams, each for excitation of one or more different ones of the compounds, directing the laser beams along a common optical path to a sample cell for containing a volume of sample gas, and detecting light output from the cell.

Features in one aspect may be applied as features in another aspect in any appropriate combination. For example, method features may be applied as system features or vice versa.

BRIEF DESCRIPTION OF THE DRAWINGS

Various aspects of the invention will now be described by way of example only and with reference to the accompanying drawings, of which.

DETAILED DESCRIPTION OF THE DRAWINGS

Figure 1:
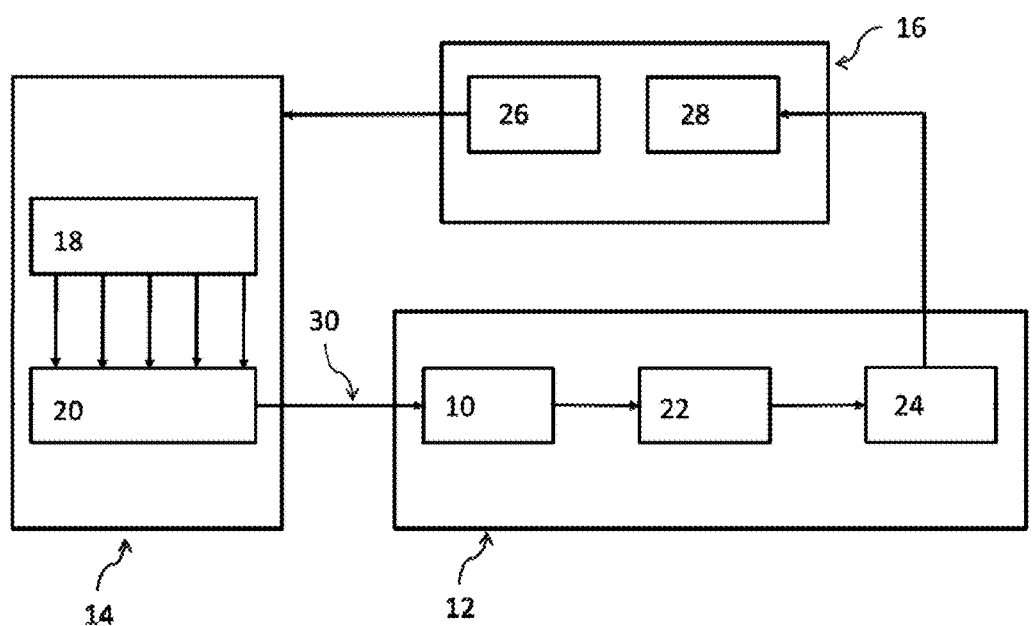
FIG. 1 is a schematic representation of a laser spectroscopy system.

FIG. 1 is a schematic representation of a laser spectroscopy system for analysing gas collected in a sample cell 10 of a sensor apparatus 12. The system comprises a laser module 14 that is optically coupled to the sensor apparatus 12. The system also includes a controller 16 that is electronically, electrically or otherwise connected to the laser module 14 and the sensor apparatus 12. The laser module 14 comprises a plurality of lasers 18 and at least one directing device in the form of a plurality of optical components 20 arranged to direct laser beams from the lasers along a common optical path into the sample cell 10, as described in more detail below in relation to FIG. 2.

In addition to the sample cell 10, the sensor apparatus 12 also includes steering optical components 22 and a detector apparatus 24 comprising a plurality of detectors. The detectors are configured to detect light from the sample cell. The light may be infra-red or visible light or light of any other suitable wavelength or from any suitable part of the electromagnetic spectrum. The controller 16 comprises a control module 26 and a signal processor 28. The control module 26 is configured to control operation of the lasers and the signal processor 28 is configured to process signals obtained from the detector apparatus 24. The controller 16 may be, for example, in the form of a suitably programmed PC or other computer, or may comprise dedicated circuitry or other hardware, for example one or more ASICs or FPGAs or any suitable mixture of hardware and software. The control module 26 and processing module may be provided as separate, distinct components in some embodiments, for example separate processing resources, rather than being provided within the same controller component as shown in FIG. 1.

The sample cell 10 has an optical entrance aperture and an optical exit aperture. The sample cell 10 may, for example, be a Herriot cell or any other suitable type of sample cell. The sample cell 10 of FIG. 1 defines a volume into which a sample of gas can be introduced and collected. The gas can comprise one or more different compounds of interest. An indication of the presence of these compounds in the gas collected in the sample cell 10 can be determined by passing light from the lasers 18 through the sample cell 10. If the light is in a wavelength range that corresponds to the absorption spectrum or absorption lines of the compound of interest, then any absorption of light as it passes through the cell may be due to the presence of the compound of interest in the sample. The level of absorption, once determined, can be used to determine a physical property of the compound of interest in the sample, for example, concentration. As different compounds have absorption spectra at different wavelength, different wavelengths of light are provided to the sample cell 10.

Figure 2:
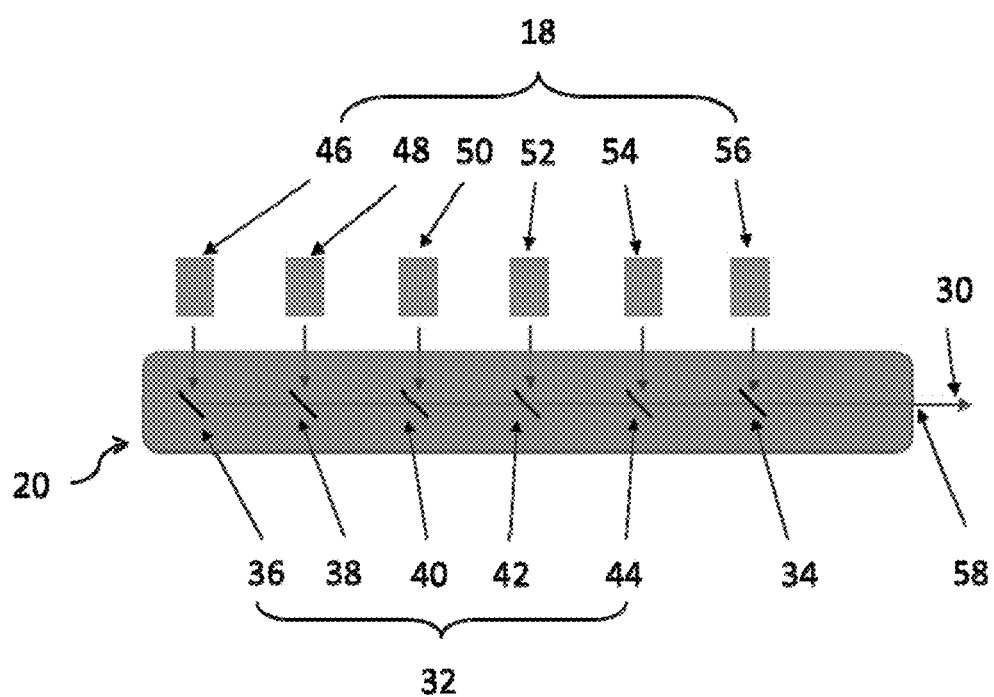
FIG. 2 is a schematic view of a laser module of the laser spectroscopy system.

FIG. 2 is a more detailed schematic view of a part of the laser module 14 of the laser spectroscopy system shown in FIG. 1. The optical components 20 comprise a set of partially reflective mirrors 32 and a dichroic mirror 34. The partially reflective mirrors 32 comprise a first mirror 36, a second mirror 38, a third mirror 40, a fourth mirror 42 and a fifth mirror 44. The lasers 18 comprise a first laser 46, a second laser 48, a third laser 50, a fourth laser 52, a fifth laser 54 and a sixth laser 56. The partially reflective mirrors 32 and the dichroic mirror 34 are configured to direct laser beams from the lasers 18 along a common optical path to point 58. Additional steering optical components to steer the combined laser beam 30 from point 58 along the common optical path to the sample cell 10 are included in the system but not shown in FIG. 2. Each of the lasers 46, 48, 50, 52, 54, 56 has a corresponding mirror 36, 38, 40, 42, 44, 34. The partially reflective mirrors 32 and the dichroic mirror 34 are arranged in a straight line. Each mirror is tilted with respect to this straight line at a 45 degree angle. The straight line defines a direction of propagation from the first mirror 36 to the dichroic mirror 34 and then to point 58. A combined laser beam 30 propagates along the direction of propagation.

Any suitable partially reflective mirrors may be used. In the embodiment of FIG. 2, each of the partially reflective mirrors comprise coated infrared $BaF_2$ or $CaF_2$ windows that have an optical coating applied to control broadband reflection of the front surface. Any other suitable materials can be used in alternative embodiments. In the embodiment of FIG. 2, two coatings are used, an 80:20 (80% transmission, 20% reflection) and a 50:50 (50% transmission, 50% reflection). This can allow the variety of laser powers to be adjusted to harmonise the output power to a consistent value for each laser (within practical limits). More or fewer coatings can be used in alternative embodiments. The coatings of the partially reflective mirrors of FIG. 2 are designed to be broadband, such that any variation in their response to a change in wavelength, particularly around wavelengths of interest, is reduced or minimised.

Any suitable dichroic mirrors may be used. In the embodiment of FIG. 2, the dichroic mirror comprises a coated infrared BaF2 window that has an optical coating applied to cause light lower than a specified wavelength to be reflected and light higher than said specified wavelength to be transmitted. Any other suitable materials can be used in alternative embodiments. In the embodiment of FIG. 2, the coating is such as to reflect light less than 1 µm in wavelength and to transmit light greater than 1 µm in wavelength.

In other embodiments, other suitable types of mirror or optical devices may be used in place of the partially reflective mirrors and the dichroic mirror. For example, in some embodiments a mirror other than a dichroic mirror or partially reflective mirror may be used at the position of dichroic mirror 34, e.g. at the last mirror position before point 58. Such a mirror may be used at the last position to introduce more power into the cell. This can be possible as or if the last position does not have any additional lasers behind it such that no lasers need to pass through the last position. In alternative embodiments, any suitable number and combination of partially reflective mirrors and dichroic mirrors may be used.

Each of the partially reflective mirrors 32 is configured to partially reflect and partially transmit light incident on it. The reflection and transmission properties of the mirror are chosen to direct laser beams from the lasers 18 along the common optical path. In the embodiment of FIG. 2, each of the partially reflective mirrors 32 reflects 20% of the incident light and transmits 80% of the incident light from the corresponding one of the lasers 18. The partially reflective mirrors 32 may have different reflection and transmission properties in alternative embodiments. The dichroic mirror 34 is defined by a reflection wavelength range and is configured to reflect light that has a wavelength in the reflection wavelength range and transmit light with a wavelength outside the reflection wavelength range. The reflection wavelength range of the dichroic mirror 34 is chosen to correspond to a wavelength range of the sixth laser 56, such that light from the sixth laser 56 is reflected and light from the first to fifth lasers is transmitted. The mirrors are flat or non-wedged optical components. Advantageously this allows the system to operate in an orthogonal fashion. For example, the system has a geometrical arrangement such that the direction of propagation from the first mirror 36 to the dichroic mirror 34 is substantially orthogonal to the laser beams output from the lasers 18.

Another advantage of using flat or non-wedged optical components in embodiments is that the directing of the laser beams to the common optical path may be substantially independent of wavelength, for example such that any distortion effects or other artefacts caused by the optical components may be substantially independent of wavelength. However, the use of mirrors may cause the resulting optical signal to be subject to fringe interference effects. These effects can be reduced by selecting the dimensions, in particular the thickness, of the optical components to control the Free Spectral Range of the system.

The Free Spectral Range is a measure of the wavelength difference between two successive maxima or minima. Typically, a suitable thickness of the optical components is less than 1 mm. This choice presents at worse a Free Spectral Range of 4 $cm^{-1}$ or greater. By controlling the Free Spectral Range, the frequency at which fringing effects occur can be shifted to not coincide and/or interfere with the measurement of the compounds in the sample cell 10.

The Free Spectral Range of this magnitude provides a spectral window that is similar in width to the spectral window covered by an entire laser scan. An expected effect is a curvature on the background of the laser pulse. This background can be easily removed using spectral fitting algorithms as part of the processing the signal. Additional fringing effects are avoided in the steering optical components 22 in the sensor apparatus 12 and optics used to steer light to the sample cell 10 through the use of non-flat or wedged optical components.

Each laser in FIG. 2 has a corresponding mirror belonging to the set of five partially reflective mirrors 32 and one dichroic mirror 34. In operation a laser beam from the first laser 46 passes to the first mirror 36 and then from the first mirror 36 to the point 58. The first mirror 36 is tilted such that the laser beam from the first laser 46 is reflected at a right angle by the first mirror 36. Likewise, each of the second to fifth lasers has a corresponding optical path defined by the second to fifth mirrors. A sixth optical path is defined in the same way from the sixth laser 56 to the dichroic mirror 34 and to the point 58. All of the mirrors are arranged at the same tilted angle as the first mirror 36 such that each of the optical paths bends at a right angle at its point of intersection with its corresponding mirror.

The mirrors are arranged such that laser beams from the lasers 46, 48, 50, 52, 54, 56 pass along a common optical path to the cell 10 via point 58 after reflection by their corresponding optical components 36, 38, 40, 42, 44, 34. The common optical path may, for example, have one end at the first mirror 36 and the other end at the entrance aperture 84 to the sample cell 10 and may extend through point 58 and when directed to pass along the common optical path, the optical paths of each respective laser joins the common optical path. Hence, the optical paths of each laser may substantially overlap.

In operation, the lasers 18 are controlled by the control module 26, or other control component in other embodiments, to sequentially produce pulses. The sequence may be as follows. The first laser 46 produces a first pulse that is directed to point 58 by the optical components and passes onward to the sample cell 10. Subsequently, the second laser 48 produces a second pulse that is directed to point 58 by the optical components and passes onward to the sample cell 10. This is followed, in turn, by a third pulse produced by the third laser 50 that is directed to point 58 by the optical components and passes onward to the sample cell 10, a fourth pulse produced by the fourth laser 52 that is directed to point 58 by the optical components and passes onward to the sample cell 10, a fifth pulse produced by the fifth laser 54 that is directed to point 58 by the optical components and passes onward to the sample cell 10, and a sixth pulse produced by the sixth laser 56 that is directed to point 58 by the optical components and passes onward to the sample cell 10. Following the sixth pulse, this sequence is repeated. The pulsed beams from each of the lasers are interleaved and/or non-overlapping in time and propagate along the common path to the sample cell 10

Following the above sequence, the first pulse is incident on, and reflected by, the first mirror 36 and is then transmitted by the second, third, fourth, fifth and dichroic mirror 34 to point 58 and continues to the sample cell 10 and the detector apparatus 24. Subsequently, the second pulse is incident on, and reflected by, the second mirror 38 and is then transmitted by the third, fourth, fifth and dichroic mirror 34 to point 58 and onward to the sample cell 10 and detector apparatus 24. Subsequently, the third pulse is incident on, and reflected by, the third mirror 40 and then transmitted by the fourth, fifth and dichroic mirror 34 to point 58 and onward to the sample cell 10 and detector apparatus 24. Subsequently, the fourth pulse is incident on, and reflected by, the fourth mirror 42 and is then transmitted by the fifth mirror 44 and the dichroic mirror 34 to point 58 and onward to the sample cell 10 and detector apparatus 24. Subsequently, the fifth pulse is incident on, and reflected by, fifth mirror 44 and is then transmitted by the dichroic mirror 34 to point 58 and onward to the sample cell 10 and detector apparatus 24. The last pulse in the sequence is the sixth pulse and this pulse is incident on and reflected by the dichroic mirror 34 to point 58 and onward to the sample cell 10 and detector apparatus 24. The pulse sequence is then repeated.

The pulses propagate through the sample cell 10 to the sensor apparatus 12. The steering optical components 22 in the sensor apparatus 12 steer light (originating from the first to fifth lasers) from the cell to a first detector that is sensitive to light from the first to fifth lasers. Thus, in this embodiment one of the detectors is sensitive to light from more than one of the lasers. The steering optical components 22 in the sensor apparatus 12 steer light (originating from the sixth laser) from the cell to a second detector that is sensitive to light from the sixth laser 56. The steering optical components 22 include a second dichroic mirror to direct light of the sixth laser 56 towards the second detector and to direct light of the first to fifth lasers to the first detector. The optical properties of the second dichroic mirror may match the properties of the dichroic mirror 34 of the laser module 14. The steering optical components 22 include two separate off-axis parabolic mirrors to focus the two different branches of light onto the two detectors. The control module synchronises operation of the lasers and the first and second detectors, such that each of the detection signals corresponds to light received from a respective one of the lasers.

The lasers 18 of FIG. 1 are semiconductor diode lasers that are operable to produce light over a sub-range of wavelengths. The lasers may be quantum cascade lasers, for example pulsed, chirped quantum cascade lasers, although any other suitable types of laser may be used in alternative embodiments. The lasers may, for example, produce beams of 2 to 3 mm in diameter, or of any other suitable size.

The sub-ranges of wavelengths may be in the infra-red spectrum. The wavelength ranges are chosen to correspond to the measurement of one or more compounds. Together the instrument may provide multiple wavelength ranges of light and combines, for example, visible, near infrared and/or mid infrared light to take advantage of the most suitable wavelengths for each compound. Table 1 shows an example implementation of wavelength ranges for lasers 18, the corresponding wavenumber range and the corresponding compound detected by light in this wavelength range:

TABLE 1

| Laser | Wavelength Range (μm) | Wavenumber Range (cm$^{-1}$) | Compounds Detected |
|---|---|---|---|
| 1 | 5.2632-5.2356 | 1900-1910 | Nitrogen Oxide (NO), Water (H2O) |
| 2 | 6.1538-6.1162 | 1625-1635 | Nitrogen Dioxide (NO2) |
| 3 | 4.4742-4.4743 | 2225-2235 | Carbon Monoxide (CO), Carbon Dioxide (CO2) |
| 4 | 7.4627-7.4349 | 1340-1345 | Methane (CH4), Sulphur Dioxide (SO2) |
| 5 | 10.0-10.2 | 980-1000 | Ammonia (NH3), Acetylene (C2H2) |
| 6 | 0.7605-0.7599 | 13150-13160 | Oxygen (O2) |

Careful selection of wavelength ranges of the lasers allows multiple measurements per laser wavelength. As can be seen in Table 1, the wavelength ranges of the first five lasers are of the same order of magnitude. However, the wavelength range of the sixth laser to detect Oxygen is an order of magnitude smaller. The first and second detectors are selected to detect light in the wavelength ranges of the first to fifth laser, or the wavelength range of the sixth detector respectively.

The control module 26 is configured to send one or more electronic control signals to the lasers 18. In response to the electronic control signals, the lasers 18 produce the combined laser beam 30. The control signal acts to pulse the lasers 18 sequentially. In other words, the control signal acts to drive each of the lasers 18 in a sequence, such that over a sample time interval only light from one laser is provided to the optical components 20. The optical components 20 are configured to direct the light from each laser along the optical path of the laser to follow the common path to the sample cell 10. In this way, the control module 26 controls the laser module 14 to produce the combined laser beam 30 and provide the combined laser beam 30 to the sample cell 10.

The switching frequency between the lasers is selected to ensure a reliable measurement in the sensor apparatus 12. In particular, the time taken for a pulse of light to traverse its sample cell optical path is dependent on the physical properties of the pulse and the dimensions of the sample cell 10. If light from more than one laser is incident in the sample cell 10 over a sample time interval then interference can occur leading to an unreliable measurement. Therefore, the pulse lengths and frequency of subsequent laser pulses are controlled and selected to take into account the time taken by light to traverse its sample cell optical path to ensure that light from only one laser is present inside the sample cell 10 over a sample time interval. Suitable pulse durations for pulses from the lasers 18 may be between 100 nanoseconds and 5000 nanoseconds. The frequency of sequential pulsing may be up to 100 kHz in some embodiments.

The signal processor 28 processes the detection signals from the detectors to determine the concentrations and/or relative amounts of the different compounds under investigation, or to determine any other desired properties. The signal processor 28 uses any suitable known processing techniques to determine the concentrations, relative amounts or other properties.

A calibration mechanism may also be provided. An example calibration mechanism comprises a camera and a mirror adjustment mechanism. The camera or is positioned at or near the point 58 to intersect a desired direction of propagation of the combined laser beam 30. The desired direction of propagation is such that the combined laser beam 30 will, in normal operation, enter the sample cell 10 via the common optical path. During a calibration step, sample beams are produced by the lasers 18 and the sample beams are directed by the optical components 20 to the camera. The camera detects the position of the sample beams incident on it relative to the desired direction of propagation. The mirror adjustment mechanism adjusts the position, in particular the tilt relative to the direction of propagation, of the partially reflective mirrors 32 and dichroic mirror 34 to substantially align the optical paths of the lasers 18 with the desired direction of propagation and substantially align the optical paths with each other. For example, the optical paths are substantially aligned within a 1.1° tolerance. The calibration step is repeated for each of the lasers 18.

Figure 3:
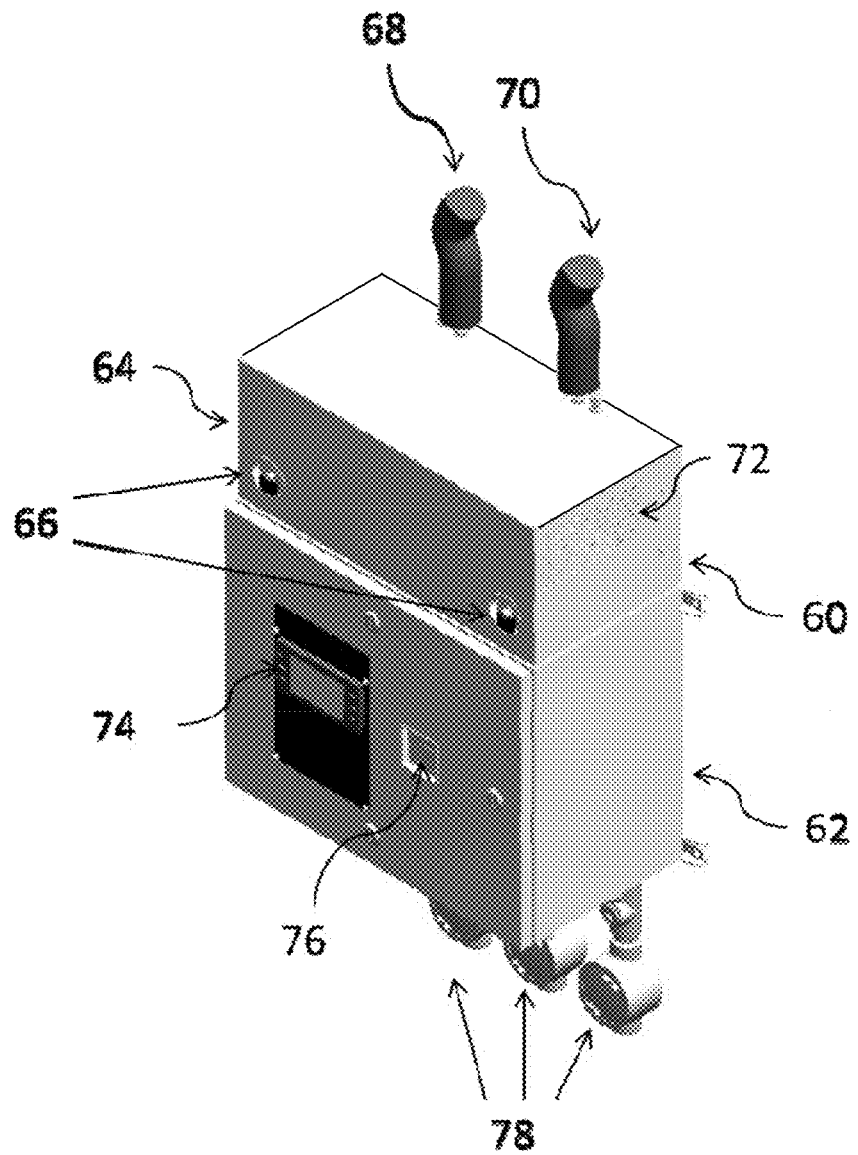
FIG. 3 is a perspective view of housing for the laser spectroscopy system.

FIG. 3 is a perspective view of housing for the laser spectroscopy system. The housing has an upper section 60 and a lower section 62. The upper section 60 has a lift-off cover 64 that is secured in a closed position by a first and second release catch 66. The sample cell 10 is located in the upper section 60 of the housing. A gas supply arrangement in the form of sample supply tube 68 provides gas to the sample cell. A sample return tube 70 provides an outlet for gas from the sample cell. Ventilation is provided to the sample cell via a vent 72 in the upper section 60. The lower section 62 has a local operator user input display 74 and a purge control display 76. In the embodiment of FIG. 3, the user input display is for interaction with the analyser and visual communication of measurements and status. Some maintenance functionality is provided by the user input display in this embodiment, however its purpose is mostly communication of measurement values and status.

The purge control display 76 of the embodiment of FIG. 3 is used control the air purge of the enclosure. This can be a requirement of hazardous area installations where steps must be taken to prevent fire hazards. In this case an air purge controlled via the purge control display 76 supplies, for example constantly supplies, the enclosure or housing of the system with clean air to prevent an explosive environment from building up.

Also connected to the lower section 62 are three output conduits 78. The conduits provide electrical breakthroughs that allow power and control signals to be sent to the system and to allow data to be transmitted from the system. The data transmitted may, for example, be in the form of digital signals, digital health signals, analogue signals for example 4-20 mA signals indicating measured values of gases, more sophisticated protocols such as Modbus, or in any other suitable format. The arrangement described above provides a compact system. In some embodiments, the housing may be around 550 cm long, the upper section may be around 200 cm tall and the lower section may be around 370 cm tall.

The sample supply tube 68 and the sample return tube 70 provides a fluid communication path through the sample cell. The sample gas can be collected from a remote location and can be delivered via the sample supply tube 68 to the sample cell to be sampled. The sample gas can then be exhausted from the sample cell via the sample return tube 70. Together, the sample supply tube 68 and the sample return tube 70 allow for the instrument to operate remotely, in contrast to in-situ emission sensing. Any other suitable gas supply arrangement may be used in alternative embodiments.

A sample handling system (SHS) unit (not shown) may be provided to control pressure of the gas in the sample cell 10. Any suitable SHS unit or other pressure control device may be used, which may or may not comprise or be driven by a pump and may or may not comprise other pressure control components such as an arrangement of valves. In the embodiment of FIG. 3, the SHS unit includes an aspirator rather than a pump, although a pump or other pressure control device or components may be used in other embodiments.

Additionally, the housing contains at least one absorber component to absorb laser light that is not directed along the common path to the sample cell 10. The at least one absorber component may contain additional optical components, for example wedged optical components.

Any suitable sample cell may be used as sample cell 10. In the embodiment of FIGS. 1 to 3, a Herriot cell is used as the sample cell. Any suitable Herriot cell may be used, or any suitable multipass spectroscopic absorption cell, or for example any other cell which is configured to provide interaction between the laser beam(s) and the sample gas, for instance by way of reflection of the laser beam between surfaces of a chamber containing the gas.

A skilled person will appreciate that variations of the described embodiments are possible without departing from the scope of the claimed invention. For example, while it is discussed that a control module in the controller is used to sequentially pulse the output of the lasers allowing the combined beam to be produced, other controller arrangements can also be used. One alternative is a mechanical optical switching arrangement that physically controls laser light such that only one laser provides light to the optical components over a given interval of time. As another example, the lasers described are semiconductor diode lasers that operate over a wavelength range. However, the lasers may be any suitable radiation source capable of providing suitable wavelengths of light. Additionally, the lasers may be single wavelength. Another example, of a modification is to replace the off-axis parabolic mirrors with any suitable focussing arrangement. Accordingly, the above description of the specific embodiments is made by way of example only and not for the purposes of limitations. It will be clear to the skilled person that minor modifications may be made without significant changes to the operations described.

The invention claimed is:

1. A laser detection system comprising:
a plurality of lasers wherein each laser is configured to produce a respective laser beam for excitation of one or more different compounds, the plurality of lasers thereby producing a plurality of laser beams;
a sample cell for containing a volume of sample gas;
at least one directing device configured to direct the plurality of laser beams to the sample cell, wherein the at least one directing device is configured to direct the plurality of laser beams along a common optical path to the sample cell;
a detector apparatus for detecting light output from the cell; and
a controller configured to control the plurality of lasers to pulse at least one of the plurality lasers, wherein the at least one directing device comprises a plurality of optical components, each optical component of the plurality of optical components corresponding to a laser of the plurality of lasers, wherein the plurality of optical components are arranged such that, for each laser beam of the plurality of laser beams its corresponding optical component is arranged to direct said laser beam along the common optical path,
wherein the plurality of optical components are arranged in series substantially along a straight line and are configured such that in operation each optical component directs the laser beam from its corresponding laser in a same direction of propagation along said straight line to join said common optical path,
wherein at least one optical component of the plurality of optical components directs or allows passage of one or more laser beam(s) of the plurality of laser beams from preceding optical component(s) in the series in the same direction of propagation along said straight line,
wherein the controller is further configured to synchronize operation of the detection apparatus and the lasers, thereby to obtain a series of detection signals, each detection signal being associated with a respective one of the lasers,
wherein each laser has a corresponding optical path from the laser to the detector apparatus via the sample cell,
wherein the optical paths of the lasers have different optical path lengths and the optical paths join to form the common optical path, and
wherein the synchronization between the lasers and the detector apparatus is dependent on at least the optical path length of each laser.

2. A system according to claim 1, wherein each of the plurality of lasers is arranged such that in operation each of the plurality of lasers transmits its laser beam to its corresponding one of the plurality of optical components in a direction substantially orthogonal to said straight line.

3. A system according to claim 1, wherein at least one of the plurality of optical components comprises a flat or non-wedged optical component.

4. A system according to claim 1, where the plurality of optical components comprise at least one partially reflective mirror and/or at least one dichroic mirror.

5. A system according to claim 1, wherein each of the plurality of optical components has a thickness in a range 0.1 mm to 1 mm.

6. A system according to claim 1, wherein each of the plurality of optical components is at least partially reflective and at least partially transmissive.

7. A system according to claim 1, wherein the at least one directing device comprises steering optics between the last of said plurality of optical components and the sample cell and configured to direct the plurality of laser beams into the optical cell.

8. A system according to claim 1, wherein the detection apparatus comprises a plurality of detectors, each detector being configured to detect radiation of a respective wavelength or range of wavelengths.

9. A system according to claim 1, wherein the controller is configured to control the plurality of lasers such that the plurality of laser beams are pulsed laser beams interleaved in time.

10. A system according to claim 9, wherein the controller is configured to control operation of the plurality of lasers such that each laser beam is pulsed at a rate in a range 1 kHz to 200 kHz, optionally in a range 10 kHz to 100 kHz, and/or wherein the controller is configured to control the plurality of lasers such that each laser beam is pulsed with pulse lengths in a range 100 ns to 5000 ns.

11. A system according to claim 1, wherein said laser beam(s) exiting a final optical component in the series of the plurality of optical components are directly incident on the sample cell.

12. A system according to claim 1, further comprising a processing resource configured to determine an amount of NOx based on the detected light outputs.

13. A system according to claim 1, wherein the one or more different compounds comprise at least one of: NO, $NO_2$, $H_2O$, CO, $CO_2$, $CH_4$, $SO_2$, $NH_3$, $C_2H_2$ and $O_2$.

14. A system according to claim 1, wherein each of the plurality of lasers is configured to produce infrared laser radiation, and wherein each optical component has one or more dimensions selected to control the Free Spectral Range of the system.

15. A system according to claim 1, wherein each of the plurality of lasers is configured to produce a laser beam of a respective different wavelength or range of wavelengths.

16. A system according to claim 15, wherein at least one of the ranges of wavelengths is selected from the following ranges: 5.2632 to 5.2356 μm; 6.1538 to 6.1162 μm; 4.4742 to 4.4743 μm; 7.4627 to 7.4349 μm; 0.7605 to 0.7599 μm; and 10.0 to 10.2 μm.

17. A system according to claim 1, wherein the detector apparatus is arranged on the opposite side of the sample cell to the plurality of lasers and the at least one directing device.

18. A system according to claim 1, further comprising a gas supply arrangement configured to supply a remote sample gas to the sample cell.

19. A system according to claim 1, wherein the sample cell comprises a Herriot cell.

20. A system according to claim 1, wherein the system is a continuous emission monitoring system.

21. A system according to claim 1, wherein the plurality of optical components are arranged at a same angle, and wherein an optical component in the plurality of optical components that is closest to the sample cell has different optical properties than remaining ones of the plurality of optical components.

22. A system according to claim 1, wherein at least one optical component in the plurality of optical components has a first coating that provides 80% transmission and 20% reflection of light, and wherein at least one other optical component in the plurality of optical components has a second coating that provides 50% transmission and 50% reflection of light.

23. A system according to claim 1, further comprising:

steering optical components downstream from the sample cell, wherein the detector apparatus comprises a first detector and a second detector, and wherein the steering optical components steer light from the sample cell that corresponds to light reflected by an optical component in the plurality of optical components that is closest to the sample cell toward the first detector, and wherein the steering optical components steer light from the sample cell that corresponds to light reflected by remaining optical components in the plurality of optical components toward the second detector.

24. A system according to claim 1, wherein the controller is configured to pulse the plurality of lasers so that light from only one laser is in the sample cell at a given time.

\* \* \* \* \*